US00PP09606P

United States Patent [19]

Leue

[11] Patent Number: Plant 9,606

[45] Date of Patent: Jul. 16, 1996

[54] IMPATIENS PLANT NAMED 'SALSA RED'

[75] Inventor: Ellen F. Leue, West Chicago, Ill.

[73] Assignee: Geo. J. Ball, Inc., West Chicago, Ill.

[21] Appl. No.: 446,556

[22] Filed: May 19, 1995

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 3,919 6/1976 Hope et al. ..... Plt./87.6

P.P. 3,930 6/1976 Hope et al. ..... Plt./87.6

*Primary Examiner*—Howard J. Locker

*Attorney, Agent, or Firm*—Burns, Doane, Swecker & Mathis

[57] ABSTRACT

A new and distinct cultivar of Impatiens plant, botanically known as *Impatiens wallerana*, and named 'Salsa Red' is provided. This new cultivar was the result of a controlled breeding program wherein a plant designated 236-1 (non-patented in the United States) was pollinated by a plant designated 32-2-1 (non-patented in the United States). The new cultivar is early blooming and forms in abundance attractive fully double red blooms. The foliage is dark green. The plant exhibits a good basal-branching character and exhibits a medium upright mounded growth habit. The new cultivar can be readily distinguished from the 'Rosebud Red' cultivar (non-patented in the United States) in view of the more compact growth habit and darker red flowers that are provided.

1 Drawing Sheet

SUMMARY OF THE INVENTION

The present invention provides a new and distinctive Impatiens plant, botanically known as *Impatiens wallerana*, and hereinafter referred to by the cultivar name 'Salsa Red'.

The new cultivar is the product of a planned breeding program. More specifically, the breeding program which resulted in the production of the new cultivar was carried out in a controlled environment during May, 1991 at Elburn, Il., U.S.A. The female parent (i.e., the seed parent) was a plant designated 236-1 (non-patented in the United States) which exhibits red semi-double flowers and dark green foliage. The male parent (i.e. the pollen parent) was a plant designated 32-2-1 (non-patented in the United States) which exhibits scarlet semi-double flowers with medium green foliage. The parentage of the new cultivar can be summarized as follows:

236-1×32-2-1.

The seeds resulting from the above pollination were sown and plantlets were obtained which were physically and biologically different from each other. Selective study resulted in the identification of a single plant of the new cultivar. This plant had distinctive fully double red blooms and initially was designated 601-2.

It was found that the new cultivar of the present invention:

(a) exhibits attractive fully double red blooms in abundance,
(b) is early blooming,
(c) forms dark green foliage,
(d) exhibits a good basal-branching character, and
(e) exhibits a medium upright mounded growth habit.

Asexual reproduction of the new cultivar by stem cuttings taken during May and September, 1993 and during October, 1994, at Elburn, Il., U.S.A., has demonstrated that the characteristics of the new cultivar as herein described are firmly fixed and are retained through successive generations of such asexual propagation.

The 'Salsa Red' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Rosebud Red' cultivar (non-patented in the United States), it is found that the new variety exhibits a more compact growth habit (e.g. approximately 12.0 to 15.0 cm. in height × approximately 17.5 to 27.0 cm. in width vs. approximately 17.0×19.0 cm. in height × approximately 29.0 to 30.0 cm. in width), and darker red flowers (i.e. Red Group 45B vs. Red Group 52A).

When plant material of the 'Salsa Red' cultivar is subjected to standard random amplified polymorphic DNA marker analysis (RAPD) using polymerase chain reaction (PCR) and a know unique set of DNA primers, it is found to exhibit a different fingerprint map when compared to that of 'Rosebud Red' cultivar which confirms its genetic distinctiveness.

Plants of the new cultivar will be marketed under the FIESTA trademark by Geo. J. Ball, Inc.

BRIEF DESCRIPTION OF THE PHOTOGRAPHS

The accompanying photographs show the new 'Salsa Red' cultivar with colors being as nearly true as it is reasonably possible to make the same in color illustrations of this character. The plants were being grown in greenhouses at West Chicago, Il., U.S.A.

FIG. 1—illustrates the general appearance of an overall plant as seen primarily from above.

FIG. 2—illustrates the general appearance of a typical floret.

DETAILED DESCRIPTION

Figure 1:
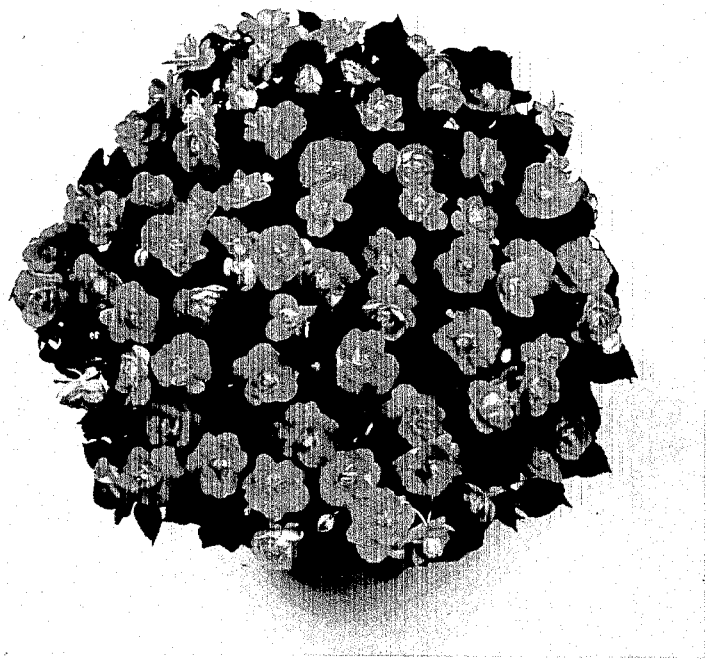
Figure 2:
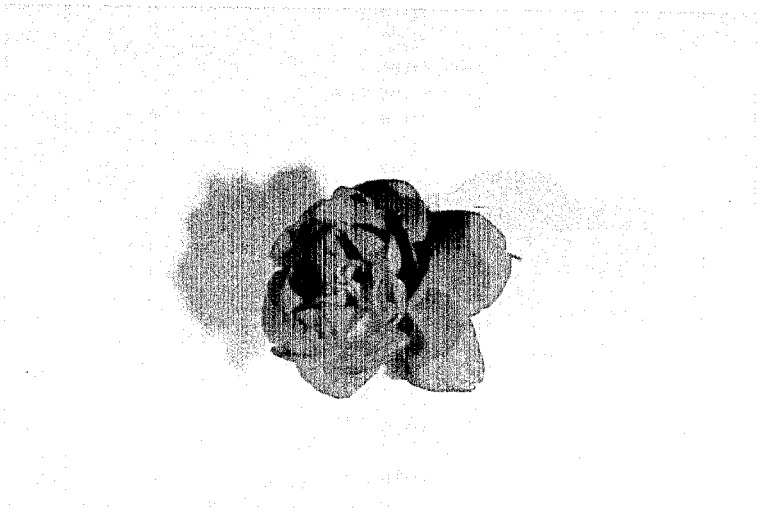

The chart used in the identification of colors described herein is The R.H.S. Colour Chart of The Royal Horticultural Society, London, England. The color values were determined on Jan. 3, 1995. The readings were taken between 10:00 and 11:00 a.m. under 2,000 footcandles of light at West Chicago, Il., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Two or three vegetative node stem cuttings from near the centers of the plants.

*Time to initiate roots.*—Approximately 7 to 14 days with the shorter times generally being experienced in the summer and the longer times in the winter.

*Rooting habit.*—Fibrous, and branching.

Plant description:

*Habit of growth.*—Basal-branching, and exhibits a medium upright mounded growth habit.

*Form.*—A mature plant at 8 weeks after the planting of a rooted cutting commonly measures approximately 12.0 to 15.0 cm. in height and approximately 17.5 to 27.0 cm. in width compared to approximately 17.0 to 19.0 cm. in height and approximately 29.0 to 30.0 cm. in width for the 'Rosebud Red' cultivar.

*Foliage.*—The configuration is ovate with an acuminate tip. The leaves of the new cultivar commonly measure approximately 4.4 to 5.6 cm. in length and approximately 3.6 to 4.4 cm. in width while those of the 'Rosebud Red' cultivar commonly measure approximately 5.9 to 6.0 cm. in length and approximately 4.0 to 4.1 cm. in width. The foliage of the new cultivar is Yellow-Green Group 146A (adaxial) and Yellow-Green Group 147C with flecks of Greyed-Purple Group 185A (abaxial). This can be compared to Yellow-Green Group 147A (adaxial) and Yellow-Green Group 147B (abaxial) for the 'Rosebud Red' cultivar. The stem color is Green Group 143B with flecks of Greyed-Purple Group 185A for both the 'Salsa Red' and 'Rosebud Red' cultivars.

Flower description:

*Flowering habit.*—Freely flowering. Small round buds become more oval with maturity and flowers open in a rose-like fashion.

*Natural flowering season.*—Early blooming and blooms throughout the year in a greenhouse environment.

*Flowers borne.*—Slightly above the foliage.

*Flower color.*—Red Group 45B on fully opened petals with the central area of tightly packed petals commonly being Red Group 45A (adaxial) and Red Group 44D (abaxial). This can be compared to Red Group 52A (adaxial) and Red Group 48C (abaxial) for the 'Rosebud Red' cultivar.

*Quantity of flowers.*—Very floriferous. A mature plant commonly is totally covered with blooms.

*Number of petals.*—Fully double and petals commonly are too numerous to readily count.

*Petal shape.*—Round to oblong.

*Flower size.*—Approximately 4.0 to 4.1 cm. in diameter for both the 'Salsa Red' and 'Rosebud Red' cultivars.

*Spur.*—One per flower of approximately 3.1 to 3.3 cm. in length which can be compared to one flower of approximately 2.5 to 3.0 cm. in length for the 'Rosebud Red' cultivar.

*Spur color.*—Closest to Yellow-Green Group 144D with a tip of Red-Purple Group 59A for both the 'Salsa Red' and 'Rosebud Red' cultivars.

*Reproductive organs.*—The stamens are multiple in number and the styles and ovaries are generally typical of the species and non-distinctive.

I claim:

1. A new and distinct cultivar of *Impatiens wallerana* plant named 'Salsa Red' substantially as herein shown and described, which:

(a) exhibits attractive fully double red blooms in abundance, (b) is early blooming, (c) forms dark green foliage, (d) exhibits a good basal-branching character, and (e) exhibits a medium upright mounded growth habit.

* * * * *